(12) United States Patent
Jaramaz et al.

(10) Patent No.: US 11,090,063 B2
(45) Date of Patent: Aug. 17, 2021

(54) CUTTING ASSEMBLY FOR USE WITH ELECTROMAGNETIC TRACKING

(71) Applicant: BLUE BELT TECHNOLOGIES, INC., Plymouth, MN (US)

(72) Inventors: Branislav Jaramaz, Pittsburgh, PA (US); Constantinos Nikou, Monroeville, PA (US); Joshua Updyke, Pittsburgh, PA (US); Ryan Sheehan, Pittsburgh, PA (US); James E. Moody, Pittsburgh, PA (US); Adam Hahn, Pittsburgh, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 215 days.

(21) Appl. No.: 16/304,354

(22) PCT Filed: May 25, 2017

(86) PCT No.: PCT/US2017/034540
§ 371 (c)(1),
(2) Date: Nov. 26, 2018

(87) PCT Pub. No.: WO2017/205664
PCT Pub. Date: Nov. 30, 2017

(65) Prior Publication Data
US 2019/0290295 A1 Sep. 26, 2019

Related U.S. Application Data

(60) Provisional application No. 62/341,347, filed on May 25, 2016.

(51) Int. Cl.
*A61B 17/16* (2006.01)
*A61B 17/32* (2006.01)
(Continued)

(52) U.S. Cl.
CPC ...... *A61B 17/1633* (2013.01); *A61B 17/1659* (2013.01); *A61B 17/32002* (2013.01);
(Continued)

(58) Field of Classification Search
CPC . A61B 17/1633; A61B 90/37; A61B 17/1615; A61B 17/32
See application file for complete search history.

(56) References Cited

U.S. PATENT DOCUMENTS

| 6,205,411 B1 | 3/2001 | DiGioia, III et al. |
| 2004/0073228 A1 | 4/2004 | Kienzle, III et al. |

(Continued)

OTHER PUBLICATIONS

International Search Report and Written Opinion for PCT/US2017/034540 dated Aug. 8, 2017.
(Continued)

*Primary Examiner* — Andrew Yang
(74) *Attorney, Agent, or Firm* — Troutman Pepper Hamilton Sanders LLP

(57) ABSTRACT

A cutting assembly (200) is configured for use with an electromagnetic tracking system (1). The cutting assembly comprises a bur assembly (10) and a sheath assembly (100). The sheath assembly comprises a sensor (135) configured to measure an electrical field around the cutting assembly, a wire (130) configured to operably connect the sensor and an external computing device (6), and a sensor mount (110) affixed to at least a portion of the sheath assembly, the sensor mount configured to house the sensor and at least a portion of the wire. The sheath assembly is configured to receive at least a portion of the bur assembly such that any impact from magnetic interference caused by, for example, a cutting device (40) within the bur assembly on the sensor is minimized when the cutting device is cutting a patient's bone.

19 Claims, 5 Drawing Sheets

(51) Int. Cl.
*A61B 34/20* (2016.01)
*A61B 17/00* (2006.01)
(52) U.S. Cl.
CPC .... *A61B 34/20* (2016.02); *A61B 2017/00039* (2013.01); *A61B 2034/2051* (2016.02); *A61B 2217/005* (2013.01)

(56) References Cited

U.S. PATENT DOCUMENTS

| | | | |
|---|---|---|---|
| 2005/0234465 | A1 | 10/2005 | McCombs et al. |
| 2008/0306380 | A1 | 12/2008 | Parchak et al. |
| 2009/0118742 | A1 | 5/2009 | Hartmann et al. |
| 2010/0234724 | A1 | 9/2010 | Jacobsen |
| 2013/0197552 | A1 | 8/2013 | O'Brien |
| 2015/0164527 | A1 | 6/2015 | Maier |

OTHER PUBLICATIONS

Chao et al. "Simulation and Animation of Musculosketal Joint System" (Nov. 1, 1993) J. Biomechanical Engineering 115(4B): 562-568.

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

DiGioia et al. "An Integrated Approach to Medical Robotics and Computer Assisted Surgery in Orthopaedics" (1995) Carnegie Mellon University 106-111.

Dillman et al. "Haptic Devices in Medical Applications" (Jun. 23, 1999) Institute for Process Control and Robotics, 1st International Workshop, Paris, France, pp. 12-22.

Freysinger et al. "A Passive-Marker-Based Optical System for Computer-Aided Surgery in Otorhinolaryngology: Development and First Clinical Experiences" (Feb. 2002) The Laryngoscope 112(2):409.

Harris et al. "Experiences with Robotic Systems for Knee Surgery" (Mar. 19-22, 1997) Springer-Verlag, London, UK 757-766.

O'Toole III et al. "Towards More Capable and Less Invasive Robotic Surgery in Orthopaedics" (1995) Computer Vision, Virtual Reality and Robotics in Medicine 905: 123-130.

Taylor et al. "An Image-Directed Robotic System for Precise Orthopaedic Surgery" (Jun. 1994) IEE Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

CUTTING ASSEMBLY FOR USE WITH ELECTROMAGNETIC TRACKING

CLAIM OF PRIORITY

This application is a U.S. national stage filing under 35 U.S.C. § 371 of International PCT Application No. PCT/US2017/034540, filed May 25, 2017, which claims the benefit of priority to U.S. Provisional Patent Application No. 62/341,347, titled "Navigated Shaver for Use with Electromagnetic Tracking," filed May 25, 2016, each of which is incorporated herein by reference in its entirety.

TECHNICAL FIELD

The present disclosure generally relates to tracking a navigated freehand surgical tool. More specifically, the present disclosure relates to minimizing interference with magnetic-based positioning of a freehand surgical tool when that tool is motorized and utilizes spinning parts.

BACKGROUND

The use of computers, robotics, and imaging to provide aid during surgery is known in the art. There has been a great deal of study and development of computer-aided navigation and robotic systems used to guide surgical procedures. For example, a precision freehand sculptor employs a robotic surgery system to assist the surgeon in accurately cutting a bone into a desired shape. In procedures such as total hip replacement (THR), computer-aided surgery techniques have been used to improve the accuracy and reliability of the surgery. Orthopedic surgery guided by images has also been found useful in preplanning and guiding the correct anatomical position of displaced bone fragments in fractures, along a good fixation by osteosynthesis.

In a typical arthroscopic procedure, a practitioner may use a navigation system, such as an optical or electromagnetic tracking system, for additional guidance so that any cuts or bone shape alterations to be made are consistent with a surgical plan. Both types of tracking systems involve the attachment of sensors to both the bone to be resected and the cutting instrument to be used by the surgeon.

When the bones in the hip joint do not move smoothly against each other or the movement is impinged, the condition can cause inflammation, pain and disability. One type of impingement, Femoroacetabular Impingement ("FAI") is a condition by which bone spurs occur in the hip joint between the acetabulum and the femoral head. Over time, this bone overgrowth can result in the tearing of the labrum and breakdown of articular cartilage (osteoarthritis). When non-invasive treatment becomes ineffective, surgery is indicated so that problematic bone can be re-shaped or a hip implant can be installed. FAI surgery is less invasive than hip replacement and involves the surgeon reshaping the problematic bone(s) rather than replacing them with an implant.

It is problematic to use optical tracking for FAI surgery, however, because the geometry of the anatomy in the hip area makes it difficult to obtain unobstructed views from the optical camera to the surgical trackers. Tracking the hip bones with an electromagnetic system, on the other hand, does not require line of sight from a camera to a tracker. Instead, it involves the use of a field generator that can be located many places near or under the surgical site and electromagnetic sensors that can be embedded in the patient's bone for the procedure. Thus, electromagnetic tracking is preferred for this type of surgery.

When using electromagnetic tracking sensors, it is desirable to have the sensor positioned close to the item or location being tracked because any error in the sensed location is magnified by the distance between the sensor and the item. Moreover, any deformation or flexion of the physical structure of the surgical instrument between the sensor and the item or location being tracked will also introduce unwanted error in the location calculation. When using a surgical shaver having a spinning bur, however, the generated magnetic field close to the bur is altered, which introduces error into the position calculation if the sensor is within the altered field. It is therefore desirable to have the sensor close enough to the item or location being tracked to minimize error caused by material deformation or distance, but far enough from the item or location being tracked to minimize any error caused by spinning metal, such as that which occurs with the use of a bur. At the same time, it is also important to minimize any error that may be introduced by the shaft that connects the bur to the motor that causes it to spin, as well as any error that may be caused by the motor itself. Accordingly, there is a need for a navigated surgical shaver that can be operated in an electromagnetic tracking system wherein all sources of error are minimized.

SUMMARY

There is provided a system comprising a cutting assembly. The cutting assembly comprises a bur assembly and a sheath assembly. The sheath assembly comprises a sensor configured to measure an electrical field around the cutting assembly, a wire configured to operably connect the sensor and the computing device, and a sensor mount affixed to at least a portion of the sheath assembly, the sensor mount configured to house the sensor and at least a portion of the wire. The sheath assembly is configured to receive at least a portion of the bur assembly such that any impact from magnetic interference caused by the bur assembly on the sensor is minimized.

In some embodiments, the bur assembly may further comprise a cutting element configured to resect at least a portion of a patient's bone.

In some embodiments, the cutting element may be positioned such that the cutting element is positioned beyond a distal tip of the sheath assembly when the bur assembly is inserted into the sheath assembly.

In some embodiments, the bur assembly may further comprise a shaft, at least one suction aperture, and a vacuum port.

In some embodiments, the shaft may be positioned such that the shaft provides a fluid connection between the at least one suction aperture and the vacuum port.

In some embodiments, the suction aperture may be configured to remove debris created by the bur assembly during bone resection.

In some embodiments, the sensor may be further configured to transmit the measured electrical field to the computing device.

In some embodiments, the system may further comprise an electromagnetic tracking system configured to track objects through an electromagnetic field. The electromagnetic tracking system may comprise an electromagnetic field generator configured to generate the electromagnetic field and the computing device.

In some embodiments, the computing device may be configured to receive the transmitted measured electrical field and determine a position of the cutting assembly within the electromagnetic field.

There is also provided a cutting assembly for use with an electromagnetic tracking system, the cutting assembly comprising a bur assembly and a sheath assembly. The sheath assembly comprises a sensor configured to measure an electrical field around the cutting assembly, a wire configured to operably connect the sensor and an external computing device, and a sensor mount affixed to at least a portion of the sheath assembly, the sensor mount configured to house the sensor and at least a portion of the wire. The sheath assembly is configured to receive at least a portion of the bur assembly such that any impact from magnetic interference caused by the bur assembly on the sensor is minimized.

In some embodiments, the bur assembly may further comprise a cutting element configured to resect at least a portion of a patient's bone.

In some embodiments, the cutting element may be positioned such that the cutting element is positioned beyond a distal tip of the sheath assembly when the bur assembly is inserted into the sheath assembly.

In some embodiments, the bur assembly may further comprise a shaft, at least one suction aperture, and a vacuum port.

In some embodiments, the shaft may be positioned such that the shaft provides a fluid connection between the at least one suction aperture and the vacuum port.

In some embodiments, the suction aperture may be configured to remove debris created by the bur assembly during bone resection.

In some embodiments, the sensor may be further configured to transmit the measured electrical field to the external computing device.

The example embodiments as described above can provide various advantages over prior techniques. For example, error introduced as a result of operation of a cutting assembly such as an electric shaver is minimized without impacting the intended operation or functionality of an electromagnetic tracking system. In particular, the geometry of the cutting assembly as described herein, along with the arrangement of the components of the cutting assembly, acts to minimize the impact of electromagnetic interference caused by a spinning bur when cutting. As such, an electromagnet sensor integrated into the cutting assembly can provide a more accurate electromagnetic field reading to the electromagnetic tracking system as compared to a cutting device where interference is not limited.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the present disclosure. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
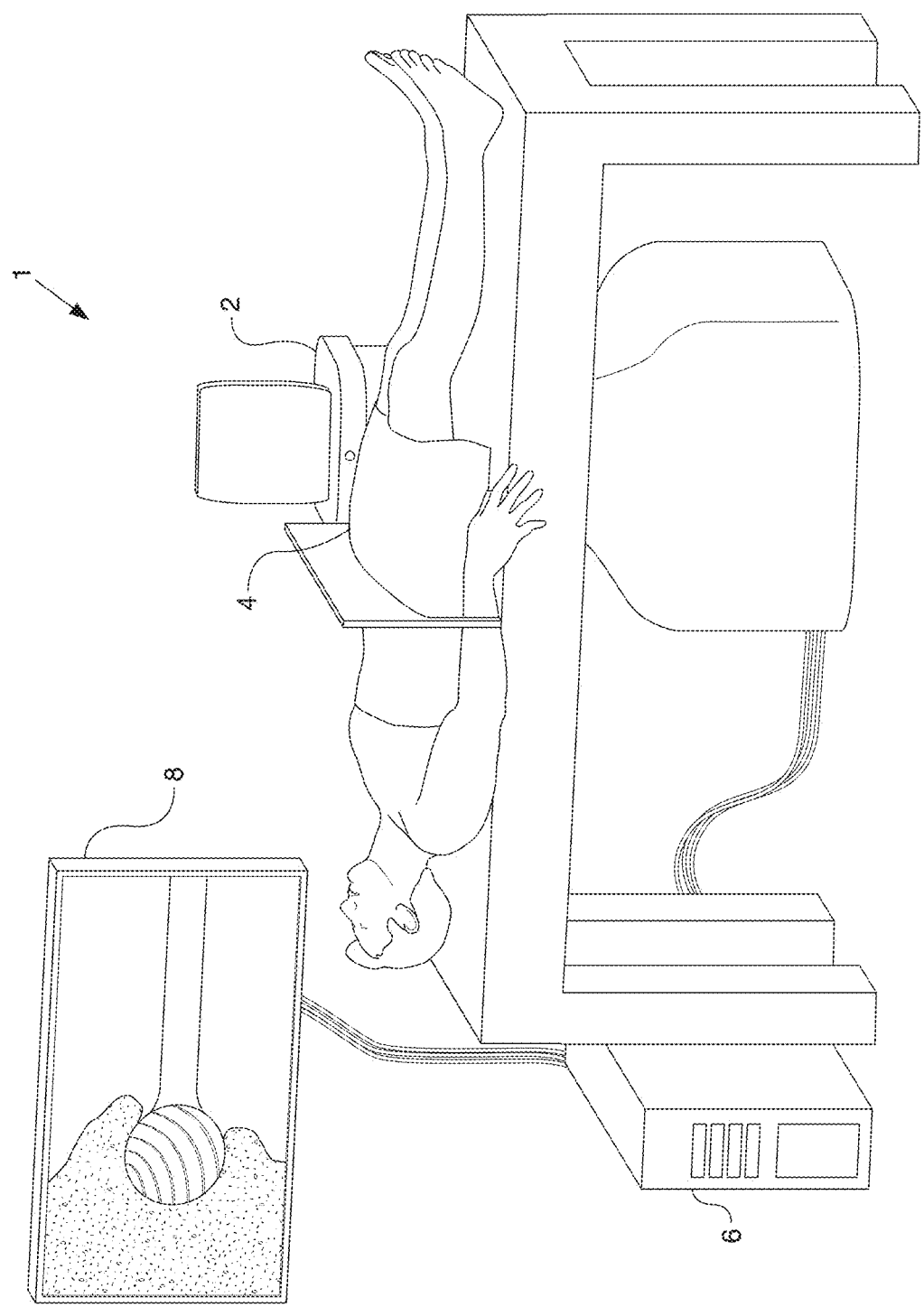
FIG. 1 depicts an illustration of an operating room with a system employing a shaver in accordance with certain embodiments of the disclosure.

Certain implementations and examples of a system used for an electromagnetically navigated FAI surgical procedure using a cutting tool such as a surgical shaver can include a handpiece, a sheath and a bur. FIG. 1 illustrates a sample electromagnetic tracking system 1. In certain implementations, the electromagnetic tracking system can include a field generator and one or more computing devices such as computing device 6. As shown in FIG. 1, in certain implementations, the field generator 2 can be placed at or near an intended surgical site 4. The field generator 2 can be configured to generate a magnetic field that extends across both the surgical site 4 and a volume of space around the surgical site referred to as the surgical space. In some examples, the field generator 2 can be an AURORA® system. AURORA is a registered trademark of NORTHERN DIGITAL, INC. of Ontario, Canada. In some examples, the frequency of the magnetic field can be about 800 hertz, about 1,600 hertz, or about 3,200 hertz. Electromagnetic field sensors, such as the AURORA Mini 6DOF Sensor from NORTHERN DIGITAL, INC., can be implanted into specific locations of the target bone or bones to be resected, such as the acetabulum or the femur. The electrical field sensors can be configured to transmit magnetic field intensity readings from each of their locations. The readings can be, for example, transmitted back to the computing device 6 that is configured to convert those field intensity readings into location values in the surgical space. Through the use of one or more computing systems, these calculated location values can then be mapped to anatomical locations on previously obtained CT scans of the patient's anatomy. The location values can also be displayed for the surgeon on a surgical monitor 8. One or more additional sensors can be placed on a cutting tool, such as a shaver, in the manner described herein such that relative positions for items within the surgical space are tracked by the system.

Figure 2:
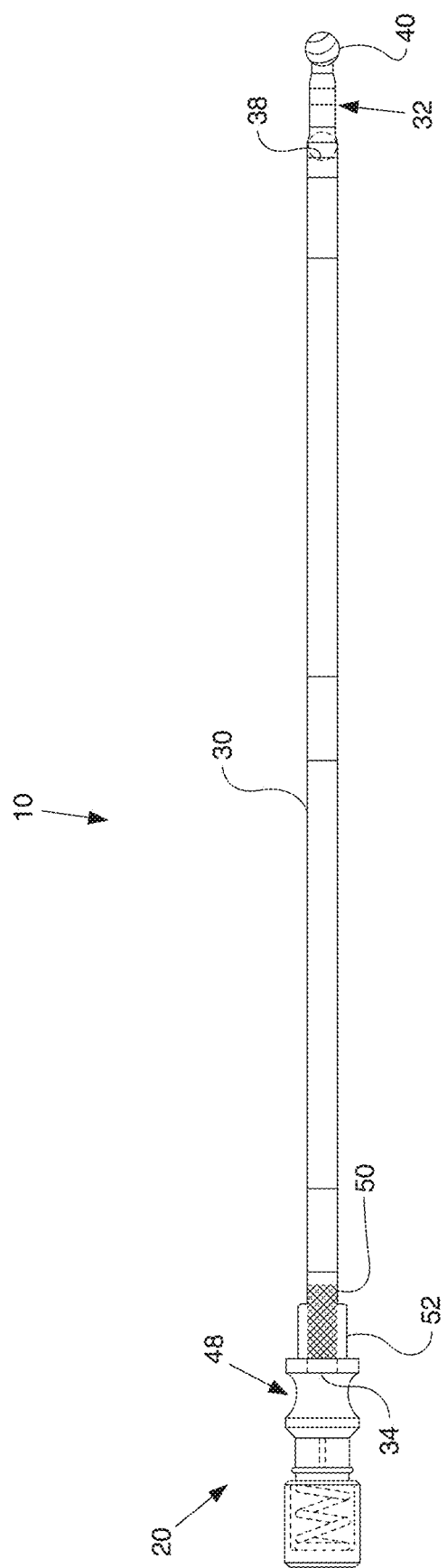
FIG. 2 depicts a side elevation view of a bur assembly constructed in accordance with certain embodiments of the present disclosure.

FIG. 2 illustrates a bur assembly 10 designed and constructed in accordance with certain embodiments of the present disclosure. As shown in FIG. 2, the bur assembly 10 can include a connector assembly 20, a shaft 30, and a cutting element 40. In certain implementations, the shaft 30 is comprised of a cobalt chrome tube or a similar material that minimizes interference with the electromagnetic tracking of the navigated shaver, such as titanium and carbon fiber. Cobalt chrome, however, is presently preferred because, not only is it stronger than stainless steel such that it is unlikely to be bent while the cutting assembly 10 is in use, it can also be welded in place of a removed stainless steel portion of the bur. In certain embodiments, then, the shaft 30 can include cobalt chrome welded at a weld point 32 to the cutting element 40. In some examples, the cutting element can be made from stainless steel. In certain implementations, the shaft measures 8.725 inches from its proximal end 34 to the distal-most point of the cutting element 40. In other implementations, the shaft can range in size from about 8 inches to about 10 inches.

Additionally or alternatively, the shaft 30 can include a suction aperture 38 positioned adjacent to or approximately adjacent to the weld point 32. The suction aperture 38 can be positioned and configured to facilitate the removal of debris and excess liquid from the surgical site. For example, during operation of the bur assembly 10, the cutting element 40 can spin at an operational or cutting speed (e.g., 50,000 to 80,000 revolutions per minute). As the cutting element 40 resects a portion of the patient's bone, various bone fragments, soft tissue fragments, and other debris can be created. The suction aperture 38 can be positioned and configured to remove this debris created by operation of the cutting element 40.

In some implementations, a plurality of suction apertures 38 that may be, for example, disposed symmetrically about the longitudinal axis of the shaft 30 such that the amount of off axis spinning material created by the cutting element 40 is more evenly distributed in order to further minimize the chance of creating interference with the electromagnetic tracking field due to moving debris.

In certain implementations, the connector assembly 20 can include a vacuum port 48 in fluid connection with the suction aperture 38 via the shaft 30. To provide the fluid connection, the shaft 30 can be configured so as to be hollow, or otherwise define a fluid channel between the vacuum port 48 and the suction aperture 38. In certain implementations, a proximal shaft section 50 can be knurled, thereby providing a textured surface to facilitate a non-slip connection with a plastic hub 52. In some examples, the plastic hub 52 can be designed as part of the connector assembly 20.

Figure 3:
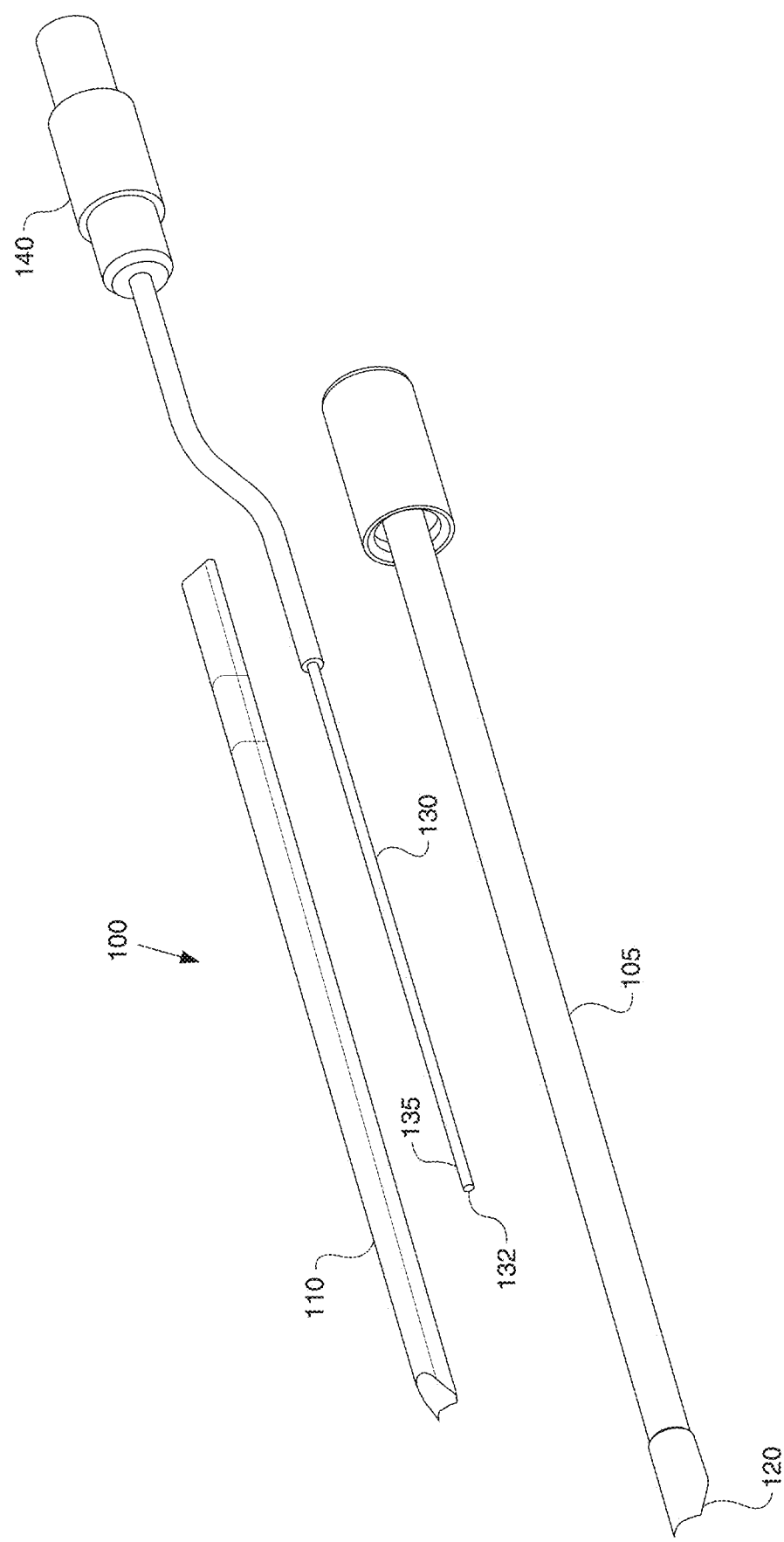
FIG. 3 is an exploded perspective view of a sheath assembly constructed in accordance with certain embodiments of the present disclosure.
Figure 4:
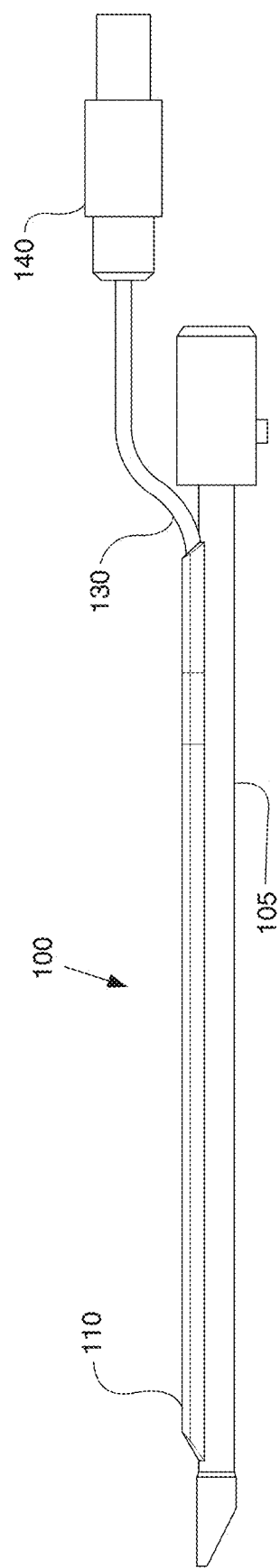
FIG. 4 depicts a perspective view of a sheath assembly constructed in accordance with certain embodiments of the present disclosure.

FIGS. 3 and 4 illustrate an exploded view and an assembled view, respectively, of a sheath assembly 100 constructed in accordance with certain embodiments of the present disclosure. In certain implementations, the sheath assembly 100 can include a sheath portion 105, a sensor wire 130, and a sensor mount 110. In certain implementations, the sheath portion 105 and the sensor mount 110 can be manufactured or otherwise constructed of a metal such as marine-grade "316" stainless steel. As such, the sheath portion 105 and the sensor mount 110 can be configured to be welded together as illustrated in FIG. 4.

In certain implementations, the sensor wire 130 can be constructed to comprise a sensor 135, such as an electromagnetic field sensor configured to measure the strength of an electromagnetic field at a particular point in space, at its distal tip 132 with lead wires (not shown) running back to a connector 140. In such a design, electrical signals generated by the sensor 135 can be sent to a system such as computing device 6. Based upon these signals, the system can calculate the precise location of the cutting element 40 in relation to the patient's anatomy. It should be noted that a sensor wire 130 is shown by way of example only as a conduit for providing the electrical signals back to the computing device. Depending upon the capabilities of the sensor and the electromagnetic tracking system, wireless communications between the sensors and the tracking system can be used.

In some implementations, the sensor mount 110 can include a groove into which the sensor 135 is fastened via, for example, an epoxy. The sensor mount 110 can then be laser welded to the sheath portion 105. In certain implementations, the sensor wire 130 can also be fixably attached to the epoxy within the sensor mount 110.

Similarly, in certain implementations, a groove can be created in the sheath portion 105 and the sensor 135 can be placed within the groove. However, rather than welding the sensor mount 110 as above, a layer of plastic or silicone could then be molded around the sheath portion 105 to form the sensor mount 110. It should be noted that welding and molding the sensor mount 110 such that the sensor 135 is affixed to the sheath portion 105 are provided by way of example only, and other means of affixing the sensor to the sheath portion will be apparent to those of skill in the art.

In certain implementations, a location of the sensor 135 in relation to the distal tip 120 of the sheath assembly 100 can be determined empirically depending on the dimensions and materials used to manufacture various components of the sheath assembly 100 and the bur assembly 10. In certain examples, the sensor 135 can disposed within the sensor mount 110, in the range of between forty (40) and seventy (70) millimeters from the distal tip 120 of the sheath assembly 100. In some implementations, the sensor 135 can be positioned between fifty (50) and sixty (60) millimeters from the distal tip 120 of the sheath assembly 100. In some examples, the sensor 135 can be positioned between fifty-four (54) and fifty-five (55) millimeters from the distal tip 120 of the sheath assembly 100.

Figure 5:
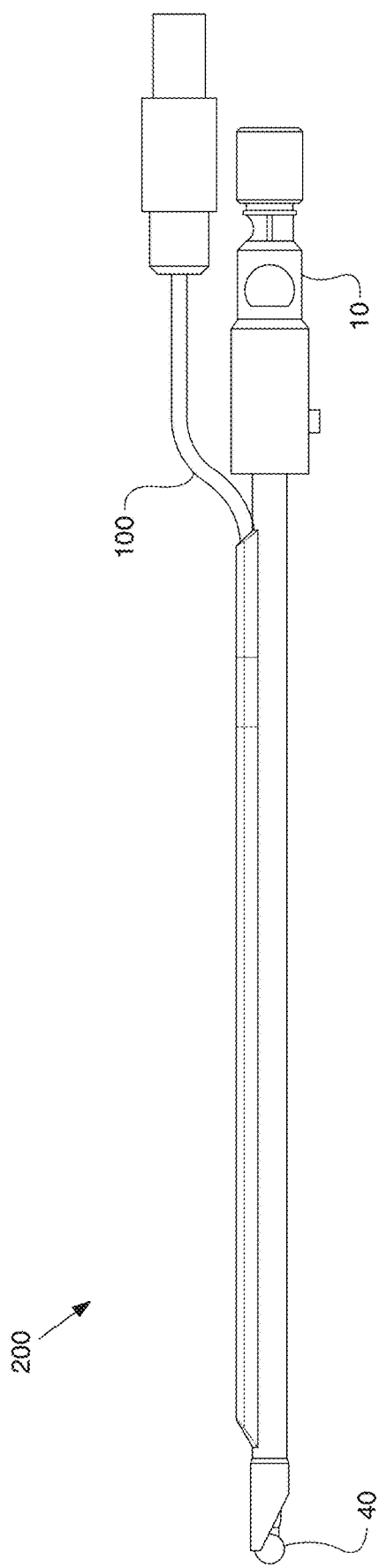
FIG. 5 depicts an illustration of a cutting assembly including the bur assembly of FIG. 2 inserted into the sheath assembly of FIGS. 3 and 4 in a manner consistent with certain embodiments of the present disclosure.

FIG. 5 illustrates a cutting assembly 200. As shown in FIG. 5, the cutting assembly 200 can include the bur assembly 10 inserted into the sheath assembly 100. As such, the sheath assembly 100 can be shaped or configured to receive at least a portion of the bur assembly 10.

As shown in FIG. 5, the cutting element 40 can be positioned such that it extends beyond the distal tip 120 of the sheath assembly 100. In use, the sheath assembly 100 can be configured to be attached to a shaver handpiece (not shown) that is capable of spinning the cutting element 40 at sufficient revolutions per minute to remove unwanted bone at the surgical site. For example, the handpiece can be configured to adjustably rotate the cutting element 40 at about 50,000 to 80,000 revolutions per minute. In certain implementations, the shaver handpiece is a Linvatec® shaver, such as the ERGO 2-button shaver handpiece D4240. LINVATEC is a registered trademark of CONMED Corporation of Albany, N.Y.

Due to the construction of the bur and the location of the sensor in relation to the bur and to the handle of the shaver handpiece, interference with the electromagnetic fields is thereby minimized. As such, the cutting device 200 as shown in FIG. 5 can be implemented into a surgical site, such as surgical site 4 as shown in FIG. 1. In such an arrangement, the cutting device 200 can be used within the electromagnetic field as generated by field generator 2. The sensor 135 (that is integrated into cutting assembly 200) can be configured to measure and transmit magnetic readings to computing device 6 as the sensor 135 passes through the field. Based upon the transmitted magnetic readings, the computing device 6 (or another similar computing system) can accurately track the position of the cutting device 200 within the surgical site 4. Additionally, as noted above, the quality and accuracy of the transmitted magnetic readings (from sensor 135) is improved as a result of, for example, the suction apertures 38 and the placement of the sensor 135 relative to the distal tip 120 of the sheath assembly 100. For example, the suction aperture 38 is configured to capture any particles of bone, soft tissue, or other debris that might interfere with the sensor 135. Additionally, the position of the sensor 135 is determined such that it is positioned a distance from the cutting element 40 that provides for a standard tool size while reducing or eliminating any electromagnetic interference caused by static or other similar electrical fields resulting from contact of the cutting element (e.g., when spinning at cutting speed) and the patient's bone.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A cutting assembly, comprising:
    a bur assembly comprising a shaft, a cutting element disposed at a distal end of the shaft, and a plurality of suction apertures disposed toward the distal end of the shaft and symmetrically about a longitudinal axis of the shaft and configured to receive debris created by the cutting element during a surgical procedure, and
    a sheath assembly comprising:
        a sensor wire comprising a distal tip and an electromagnetic (EM) field sensor disposed at the distal tip and configured to measure a strength of an EM field, wherein the sensor wire is coupled to a connector configured to operably connect the EM field sensor and a computing device via the sensor wire,
        a sheath portion disposed between at least a portion of the shaft and the sensor when the shaft is inserted into the sheath portion, and
        a sensor mount affixed to the sheath portion, wherein the sensor mount is configured to house the EM field sensor and at least a portion of the sensor wire between the sensor mount and the sheath portion.

2. The cutting assembly of claim 1, wherein the sheath portion comprises a groove in which the EM field sensor is disposed and the sensor mount comprises a non-metallic layer molded around the EM field sensor in the groove.

3. The cutting assembly of claim 1, wherein at least a portion of the cutting element is positioned beyond another distal tip of the sheath portion when the bur assembly is inserted into the sheath assembly.

4. The cutting assembly of claim 1, further comprising a vacuum port disposed toward a proximal end of the bur assembly, wherein the shaft provides a fluid connection between the plurality of suction apertures and the vacuum port.

5. The cutting assembly of claim 1, wherein the EM field sensor is further configured to transmit the measured EM field strength to the computing device via the sensor wire and the connector.

6. The cutting assembly of claim 1, wherein the shaft further comprises a connector assembly and a proximal section disposed toward the connector assembly, wherein the connector assembly comprises a plastic hub and the proximal section comprises a textured surface and is configured to connect to the proximal section.

7. The cutting assembly of claim 1, wherein the bur assembly further comprises a weld point at which the cutting element is welded to the shaft, wherein the weld point is between the cutting element and the plurality of suction apertures.

8. A cutting assembly, comprising:
    a bur assembly comprising:
        a shaft comprising a connector assembly and a proximal section disposed toward the connector assembly, wherein the connector assembly comprises a plastic hub and the proximal section comprises a textured surface and is configured to connect to the proximal section, and
        a cutting element disposed at a distal end of the shaft, and
    a sheath assembly comprising:
        a sensor wire comprising a distal tip and an electromagnetic (EM) field sensor disposed at the distal tip and configured to measure a strength of an EM field, wherein the sensor wire is coupled to a connector configured to operably connect the EM field sensor and a computing device via the sensor wire,
        a sheath portion disposed between at least a portion of the shaft and the sensor when the shaft is inserted into the sheath portion, and
        a sensor mount affixed to the sheath portion, wherein the sensor mount is configured to house the EM field sensor and at least a portion of the sensor wire between the sensor mount and the sheath portion.

9. The cutting assembly of claim 8, wherein the sheath portion comprises a groove in which the EM field sensor is disposed and the sensor mount comprises a non-metallic layer molded around the EM field sensor in the groove.

10. The cutting assembly of claim 8, wherein at least a portion of the cutting element is positioned beyond another distal tip of the sheath portion when the bur assembly is inserted into the sheath assembly.

11. The cutting assembly of claim 8, wherein the bur assembly further comprises a suction aperture disposed toward the distal end of the shaft and configured to receive debris created by the cutting element during a surgical procedure.

12. The cutting assembly of claim 11, further comprising a vacuum port disposed toward a proximal end of the bur assembly, wherein the shaft provides a fluid connection between the suction aperture and the vacuum port.

13. The cutting assembly of claim 8, wherein the EM field sensor is further configured to transmit the measured EM field strength to the computing device via the sensor wire and the connector.

14. The cutting assembly of claim 11, wherein the bur assembly further comprises a weld point at which the cutting element is welded to the shaft, wherein the weld point is between the cutting element and the suction aperture.

15. A cutting assembly, comprising:
    a bur assembly comprising:
        a shaft,
        a cutting element disposed at a distal end of the shaft,
        a suction aperture disposed toward the distal end of the shaft and configured to receive debris created by the cutting element during a surgical procedure, a weld point at which the cutting element is welded to the shaft, wherein the weld point is between the cutting element and the suction aperture, and a sheath assembly comprising:
- a sensor wire comprising a distal tip and an electromagnetic (EM) field sensor disposed at the distal tip and configured to measure a strength of an EM field, wherein the sensor wire is coupled to a connector configured to operably connect the EM field sensor and a computing device via the sensor wire,
- a sheath portion disposed between at least a portion of the shaft and the sensor when the shaft is inserted into the sheath portion, and
- a sensor mount affixed to the sheath portion, wherein the sensor mount is configured to house the EM field sensor and at least a portion of the sensor wire between the sensor mount and the sheath portion.

16. The cutting assembly of claim 15, wherein the sheath portion comprises a groove in which the EM field sensor is disposed and the sensor mount comprises a non-metallic layer molded around the EM field sensor in the groove.

17. The cutting assembly of claim 15, wherein at least a portion of the cutting element is positioned beyond another distal tip of the sheath portion when the bur assembly is inserted into the sheath assembly.

18. The cutting assembly of claim 15, further comprising a vacuum port disposed toward a proximal end of the bur assembly, wherein the shaft provides a fluid connection between the suction aperture and the vacuum port.

19. The cutting assembly of claim 15, wherein the EM field sensor is further configured to transmit the measured EM field strength to the computing device via the sensor wire and the connector.

* * * * *